United States Patent [19]
Rotramel

[11] Patent Number: 5,275,125
[45] Date of Patent: Jan. 4, 1994

[54] ANIMAL HARBORAGES

[76] Inventor: George L. Rotramel, 1292 Bauer Rd., Naperville, Ill. 60563

[21] Appl. No.: 734,969

[22] Filed: Jul. 24, 1991

[51] Int. Cl.⁵ .................... A01K 1/00; A01M 1/02
[52] U.S. Cl. ..................... 119/15; 119/156; 43/131
[58] Field of Search ............ 119/6.5, 15, 156; 43/131

[56] References Cited

U.S. PATENT DOCUMENTS

| | | | |
|---|---|---|---|
| 1,566,199 | 12/1925 | Gaskins Jr. . | |
| 1,921,945 | 8/1933 | Robertson | 43/131 X |
| 2,328,590 | 9/1943 | Weil | 43/131 |
| 2,328,591 | 9/1943 | Weil | 43/131 |
| 2,340,255 | 1/1944 | Weil | 43/131 |
| 2,340,256 | 1/1944 | Weil | 43/131 |
| 2,956,366 | 10/1990 | Wiesmann | 43/131 |
| 3,561,402 | 2/1971 | Ishida et al. | 119/3 |
| 3,704,539 | 12/1972 | Alvarez | 43/131 |
| 3,864,867 | 2/1975 | Dry | 43/131 |
| 3,996,348 | 12/1976 | Greenberg | 43/131 X |
| 4,044,495 | 8/1977 | Nishimura et al. | 43/121 |
| 4,048,747 | 9/1977 | Shanahan et al. | 43/114 |
| 4,350,122 | 9/1982 | Shotwell | 119/156 X |
| 4,395,842 | 8/1983 | Margulies | 43/114 |
| 4,400,905 | 8/1983 | Brown | 43/132.1 |
| 4,619,011 | 10/1986 | Willis | 43/131 |
| 4,630,392 | 12/1986 | Ferraro | 43/131 |
| 4,637,162 | 1/1987 | Sherman | 43/131 |
| 4,660,320 | 4/1987 | Baker et al. | 43/131 |
| 4,768,305 | 9/1988 | Sackett | 43/61 |
| 4,769,942 | 9/1988 | Copenhaver Sr. | 43/61 |
| 4,947,791 | 8/1990 | Laier et al. | 119/3 |
| 5,119,586 | 6/1992 | Townsend | 43/131 X |

FOREIGN PATENT DOCUMENTS 1373383  2/1988  U.S.S.R. .................. 119/3

OTHER PUBLICATIONS

Mizuno and Tsuji 1974, Jap. J. Sanit. Zool. Vol. 24, No. 3, pp. 237-240.

*Primary Examiner*—Robert P. Swiatek

[57] ABSTRACT

Use of porous solids having a multiplicity of external and internal openings as harborages for crawling animals. The harborages are readily fabricated and are extremely attractive to crawling insects such as cockroaches and ants and to small crawling mammals such as rats, mice and hamsters. The harborages are particularly effective as traps for the control of insect and rodent pests and as habitats for pet rodents.

3 Claims, 1 Drawing Sheet

ANIMAL HARBORAGES

BACKGROUND OF THE INVENTION

The present invention is directed generally to the use of porous solids as harborages for crawling terrestrial animals such as roaches, ants, and mice, and more particularly to the use of porous solids comprising a three dimensional array of cages connected to each other in such a manner as to present said terrestrial animals with a minimum of three alternative openings whenever said terrestrial animals are in contact with said harborages.

THE PRIOR ART

Harborages in the forms of bait stations and sticky traps are employed by homeowners, professional pest control technicians and other persons who are interested in the control of roaches, rats, mice and other crawling vermin. These pest control harborages of the known art offer the advantages of decreased hazard to man, pets and the environment; sticky traps use no pesticides at all, and bait stations use a very small amount of pesticide which is enclosed in a relatively tamper-proof metal or plastic housing. However, despite their advantages of safety and convenience, pest control harborages of the prior art are relatively unattractive to the target animals in the limited range of physical environments in which they can be used and are therefore little used in comparison to more common, but potentially more hazardous pest control methods such as spraying, dusting and the application of loose baits. There is therefore a need for a pest control harborage with a broader range of applications and greater acceptability to target animals in the terrestrial environment.

Harborages for crawling terrestrial animals are also employed in the pet industry, particularly as tubular artificial habitats for hamsters, rats, mice and the like. These artificial habitats have the advantages of being transparent and permitting easy observation of pets as they crawl through them. However, these tubular artificial habitats are difficult to clean, are limited in their organizational complexity and soon cease to stimulate exploratory activity in hamsters and other pets. When the exploratory activity of the pets decreases, the entertainment value of the pets is thereby lessened.

There is therefore a need for an artificial habitat for hamsters, rats, mice and the like that is easy to clean and which can be arranged in structures of sufficient and varying complexity as to continue to stimulate exploratory activity in hamsters and other pets for a longer period of time, thereby increasing the entertainment value of the pets for their owners.

Heretofore, artificial harborages intended for crawling terrestrial animals have been constructed in the forms of bait stations, traps or tubular habitats. These harborages of the prior art have the disadvantages of presenting target animals with only a few rigid openings through which the animals must pass in order to enter the interior of the harborage. Animals which explore the exteriors of harborages of the known art encounter only one or two alternative openings at any one time. Terrestrial crawling animal harborage designs of the prior art do not anticipate a harborage constructed according to the present invention which is comprised of a porous solid and which presents the target animals with a choice of several discrete openings through which the animals may attempt to enter the harborage when they explore the harborage from without.

Furthermore, terrestrial crawling animal harborage designs of the prior art do not anticipate a harborage constructed according to the present invention which invention presents target animals with a sequence of discrete openings arranged in a manner that allows the target animals to perceive a series of openings arranged at increasing distances from their bodies whether the target animals are inside or outside the harborage.

Surprisingly, cockroaches were observed to use their antennae to reach inside harborages of the present invention and to explore openings at depths within the harborage equivalent to one to several body lengths of the target animals. This exploratory behavior demonstrates the surprising attractiveness of a complex array of openings presented at a variety of angles by a harborage of the present invention, which openings can be readily explored by the sensory organs of crawling animals. Examples of such sensory organs of crawling animals are the antennae, mouthparts, legs and cerci of insects; and the vibrissae, guard hairs and tails of mice and other rodents.

In addition, harborage designs of the prior art do not anticipate a harborage constructed according to the present invention which allows the harborage to be used in high temperature environments.

Moreover, harborage designs of the prior art do not anticipate a flexible harborage constructed according to the present invention which is useful in irregular spaces and around moving parts of machinery, motorized equipment and the like.

When used in pest control, harborages of the known art typically contain a solid or liquid toxic bait in an interior tray or chamber. Alternatively, they may have an adhesive or toxicant on their internal surfaces. The toxicants used in harborages of the prior art are intended to control the pest animals themselves and, in some embodiments, to control parasites of the pest animals. It will therefore be understood by those skilled in the art of pest control that harborages of the present invention may be used in conjunction with biologically active agents belonging to the group consisting of adhesives, attractants, toxicants, sterilants, growth regulators, pheromones, parasiticides, nematodes, viruses, bacteria and fungi.

IMPORTANCE OF ENTRANCES

Bait stations of the prior art intended for roaches and other crawling arthropods have been constructed with up to six entrances, all of which are in the same plane. Bait stations and tubular habitats of the prior art intended for rats, mice and other small mammals have been constructed with from one to several entrances.

Stations of the prior art which employ a single large entrance have the advantage of allowing target animals to enter from a wide variety of directions but are nevertheless surprisingly unattractive to target animals. Accordingly, artificial harborages or stations of the prior art which are constructed with smaller entrances have entrances which are individually more attractive than the entrances of stations with single large entrances. However, stations of the known art with small entrances are nevertheless rendered relatively ineffective by the restrictions which a small number of entrances places on the directions from which the stations may be entered by target animals.

Despite the fact that the foregoing facts are well known to those skilled in the art, harborages of the prior art have not been designed to provide a high level of attractiveness to target animals approaching them from a wide range of directions.

Moreover, harborages constructed according to the prior art do not anticipate a harborage of the present invention which is highly attractive to target animals approaching from a wide range of directions.

In addition, harborages of the prior art fail to lure target animals away from naturally occurring harborages such as cracks, crevices and the like without the use of chemical attractants.

Furthermore, harborages of the prior art require the use of adhesives, baits, arrestants and the like in order to encourage animals to remain inside for more than a brief time.

Typical of rodent bait stations of the prior art are those described in U.S. Pat. No. 4,619,071 to Willis, 1986 Oct. 28, in U.S. Pat. No. 4,637,162 to Sherman, 1987 Jan. 20, and in U.S. Pat. No. 4,660,320 to Baker et al, 1987 Apr. 28 each of which present only two openings through which rodents may enter. U.S. Pat. No. 4,769,942 to Copenhaver 1988 Sep. 13, U.S. Pat. No. 4,768,305 to Sackett 1988 Sep. 6 and U.S. Pat. No. 4,630,392 to Ferraro 1986 Dec. 23 present only one small opening through which rodents may enter.

Typical of roach bait stations of the prior art are U.S. Pat. No. 4,048,747 to Shanahan et al 1977 Sep. 20 which describes a trap suitable for mounting along the bottom of a wall and having only a single exterior opening running in a straight line along its lower side, U.S. Pat. No. 3,704,539 to Alvarez 1972 Dec. 5 which describes a station with only a single exterior opening running around its circumference. Typical examples of roach harborages having more than one exterior opening are given in U.S. Pat. No. 2,328,590 to Weil 1943 Sep. 7, U.S. Pat. No. 2,328,591 to Weil 1943 Sep. 7, U.S. Pat. No. 2,340,255 to Weil 1944 Jan. 25, U.S. Pat. No. 2,340,256 to Weil 1944 Jan. 25 and U.S. Pat. No. 4,696,127 to Dobbs 1987 Sep. 29 which describe stations with two openings, U.S. Pat. No. 4,400,905 to Brown 1983 Aug. 30 which describes a station with two or three openings, U.S. Pat. No. 4,044,495 to Nishimura et al 1977 Aug. 30 which describes a station with two or four openings, and U.S. Pat. No. 1,566,199 to Gaskins 1925 Dec. 15 which describes a station with four openings.

U.S. Pat. No. 4,350,122 to Shotwell 1982 Sep. 21 describes a tubular collar with various arrangements of openings along its interior margin and intended as a non-toxic trap for fleas on dogs, cats and the like. None of the embodiments of the device described in U.S. Pat. No. 4,350,122 to Shotwell 1982 Sep. 21 offers target animals a series of alternative openings arranged in depth as do harborages of the present invention. Therefore, target animals entering or inside a harborage of type described in U.S. Pat. No. 4,350,122 to Shotwell 1982 Sep. 21 are only able to perceive one opening or entrance at any one time instead of the multiple openings or entrances that can be perceived by target animals entering or inside a harborage of the present invention. Furthermore, U.S. Pat. No. 4,350,122 to Shotwell 1982 Sep. 21 does not anticipate the importance of the relationship between the size of the openings and the effective exploring distances of the target animals as described in the present invention. Moreover, U.S. Pat. No. 4,350,122 to Shotwell 1982 Sep. 21 does not anticipate use of the disclosed harborage as an artificial habitat for pet rodents. Finally, U.S. Pat. No. 4,350,122 to Shotwell 1982 Sep. 21 does not anticipate the value of terrestrial animal harborages of the present invention in high temperature environments.

U.S. Pat. No. 4,947,791 to Laier et al 1990 Aug. 14 describes a system of flexible, buoyant devices suitable for use as artificial reefs for fish. The devices disclosed in U.S. Pat. No. 4,947,791 to Laier et al 1990 Aug. 14 are not intended to be in contact with the substrate and are therefore not suitable for attraction of crawling animals such as roaches, ants and rodents as are the harborages of the present invention. Furthermore, the devices disclosed in U.S. Pat. No. 4,947,791 to Laier et al 1990 Aug. 14 are unstable and will move in response to water currents, thereby making them less attractive to crawling animals than harborages of the present invention which are firmly fixed on the substrate. Moreover, the devices disclosed in U.S. Pat. No. 4,947,791 to Laier et al 1990 Aug. 14 are comprised of plastics materials and are therefore not suitable for use in high temperature environments as are the harborages of the present invention. Furthermore, those skilled in the art of pest control will appreciate that adhesives will run out of the devices described in U.S. Pat. No. 4,947,791 to Laier et al 1990 Aug. 14 much more easily, for example under conditions of high temperature or high humidity, than the same adhesives will run out of the more porous harborages of the present invention. Those skilled in the art of pest control will further appreciate that the loss of adhesive from the devices described in U.S. Pat. No. 4,947,791 to Laier et al 1990 Aug. 14 will render the devices ineffective in pest control and will contaminate the substrate with unwanted adhesive. In addition, U.S. Pat. No. 4,947,791 to Laier et al 1990 Aug. 14 does not anticipate the important relationship between the sizes of openings into and out of the device and the effective exploratory distance of the animals it is intended to harbor. Furthermore, the devices disclosed in U.S. Pat. No. 4,947,791 to Laier et al 1990 do not anticipate the importance of thigmotaxis to the attractiveness of such devices to crawling animals as is described in connection with harborages of the present invention. Finally, the devices disclosed in U.S. Pat. No. 4,947,791 to Laier et al 1990 Aug. 14 do not anticipate use for control of crawling animals such as insects and rodents or use as harborages for pet rodents as is described for harborages of the present invention.

U.S. Pat. No. 3,561,402 to Ishida et al 1971 Feb. 9 describes an elongate tubular artificial reef for fish comprised of various arrangements of perforated plates loosely held together by rings. The loose fitting rings which connect the porous plates of the devices described in U.S. Pat. No. 3,561,402 to Ishida et al 1971 Feb. 9 allow these plates to be moved by water currents or by the activity of animals crawling over them, thereby making the devices described in U.S. Pat. No. 3,561,402 to Ishida et al 1971 Feb. 9 less attractive to such crawling animals than are the stable harborages of the present invention. Furthermore, the porous plates and rings of the devices described in U.S. Pat. No. 3,561,402 to Ishida et al 1971 Feb. 9 are not suitable for use with adhesives as are the harborages of the present invention. Those skilled in the art of pest control will recognize that adhesives will be much more likely to run out of the structures illustrated in U.S. Pat. No. 3,561,402 to Ishida et al 1971 Feb. 9, for example under conditions of high temperatures or high humidity, than the same adhesives would be likely to run out of the more porous harborages of the present invention. Those skilled in the art of pest control will appreciate that the loss of adhesive from the structures illustrated in U.S. Pat. No. 3,561,402 to Ishida et al 1971 Feb. 9 will render the structures ineffective in controlling pests and will contaminate the substrate with unwanted adhesive. Moreover, addition of an adhesive to the interior surfaces of the device in FIG. 3 of Ishida et al 1971 Feb. 9, would prevent opening and use of the device. In addition, U.S. Pat. No. 3,561,402 to Ishida et al 1971 does not anticipate the important relationship between the sizes of openings into and out of the device and the effective exploratory distance of the animals it is intended to harbor. Furthermore, the devices disclosed in U.S. Pat. No. 3,561,402 to Ishida et al 1971 do not anticipate the importance of thigmotaxis to the attractiveness of such devices to crawling animals as is described in connection with harborages of the present invention. Finally, the devices disclosed in U.S. Pat. No. 3,561,402 to Ishida et al 1971 do not anticipate use for control of crawling animals such as insects and rodents or use as harborages for pet rodents as is described for harborages of the present invention.

U.S. Pat. No. 3,864,867 to Dry 1975 Feb. 11 describes a cylindrical pest control device for both roaches and rodents having as many as twenty diamond-shaped openings arranged in three tiers around its circumference. However, the device disclosed in U.S. Pat. No. 3,864,867 to Dry 1975 Feb. 11 was intended only as a holder for poison baits and fumigants and does not envision use of the device as a station for arthropods and rodents. Furthermore, the device disclosed in U.S. Pat. No. 3,864,867 to Dry 1975 Feb. 11 does not envision use of the device as a habitat for rodents. Moreover, unlike harborages of the present invention which offer target animals an array of openings arranged in depth, the device described in U.S. Pat. No. 3,854,867 to Dry 1975 Feb. 11 presents only one layer of openings to the target animals. Furthermore, only certain of the openings in the embodiments described in U.S. Pat. No. 3,864,867 to Dry 1975 Feb. 11 were envisioned as being of a size sufficient to permit an animal standing outside the container to reach a poison bait inside. Moreover, unlike harborages of the present invention which offer target animals an array of openings arranged in depth, the device described in U.S. Pat. No. 3,854,867 to Dry 1975 Feb. 11 presents only one layer of openings to the target animals.

U.S. Pat. No. 3,996,348 to Greenberg 1976 Dec. 7 describes a device formed as a flat solid with a porous surface which is not intended to be a harborage for animals, but is instead intended to release a pesticidally effective amount of a gas into the surrounding air. Unlike harborages of the present invention which offer target animals an array of openings arranged in depth, the device described in U.S. Pat. No. 3,996,348 to Greenberg 1976 Dec. 7 presents only one layer of openings to the target animals. Furthermore U.S. Pat. No. 3,996,348 to Greenberg 1976 Dec. 7 does not anticipate any contact between the pores of the device and the target animals, whether as a harborage as is described in devices of the present invention or otherwise. Finally, the device described in U.S. Pat. No. 3,996,348 to Greenberg 1976 Dec. 7 does not allow a target animal which has entered the device to perceive more than one additional orifice as is described in devices of the present invention.

U.S. Pat. No. 1,921,945 to Robertson 1933 Aug. 8 describes an irregularly shaped solid body comprised of blast furnace slag and which contains many pores on its surface which are suitable sites for settling of oyster spat. As FIG. 1 of U.S. Pat. No. 1,921,945 to Robertson 1933 Aug. 8 illustrates, the purpose of the pores on the blast furnace slag is to serve as attachment points for the developing oysters which rest on the surface of the slag and do not enter the pores. It will be clear to those skilled in the art of oyster culture that the pores in the slag are not suitable as a harborage for the developing oysters for if the developing larvae were to settle in the pores they would not have sufficient space to grow and reproduce. It is therefore clear that although equipped with surface pores, the slag in U.S. Pat. No. 1,921,945 to Robertson 1933 Aug. 8 is not intended as a harborage for animals and does not anticipate a porous harborage for crawling animals as is described in the present invention. In addition, those skilled in the art of oyster culture will understand that the porous solid described in U.S. Pat. No. 1,921,945 to Robertson 1933 Aug. 8 is not intended to attract crawling animals as are the harborages of the present invention, but is instead intended to retain swimming oyster larvae which settle on it at random after reaching the appropriate stage of morphological development. Furthermore, FIG. 3 of U.S. Pat. No. 1,921,945 to Robertson 1933 Aug. 8 shows that the pores of the blast furnace slag do not connect with each other to form internal cages as is described in harborages of the present invention. Moreover, porous solids of the type described in U.S. Pat. No. 1,921,945 to Robertson 1933 Aug. do not allow target animals to perceive three or more alternative openings after entering the porous solid as is the case in harborages of the present invention. Finally, U.S. Pat. No. 1,921,945 to Robertson 1933 Aug. 8 does not anticipate use of the disclosed device for control of crawling insects and rodents and as an artificial habitat for pet rodents.

U.S. Pat. No. 2,340,256 to Weil 1944 Jan. 25 describes an elongate rectangular station with a single opening at each end and containing an interior mass of twisted fibers such as animal fibers, straw and metal shavings which is held within the station by an adhesive. Although U.S. Pat. No. 2,340,256 to Weil 1944 Jan. 25 describes a station which presents multiple openings to animals once they have entered the station, the device described in U.S. Pat. No. 2,340,256 to Weil 1944 Jan. 25 presents only two large external openings to animals inspecting it from outside. In addition, the adhesive used to stabilize the internal fibers described in U.S. Pat. No. 2,340,256 to Weil 1944 Jan. 25 allows the fibers to shift or compress when roaches and other animals walk on them, thereby reducing the stability of the fiber mass and its attractiveness as a harborage. Furthermore, the fiber mass described in U.S. Pat. No. 2,340,256 to Weil 1944 Jan. 25 does not offer exploring animals a series of alternative openings arranged in depth as do harborages of the present invention. Finally, U.S. Pat. No. 2,340,256 to Weil 1944 January 25 does not anticipate use of the disclosed harborage for control of crawling insects and rodents and as an artificial habitat for pet rodents.

Soviet patent SU 1,373,383-A to Pacific Fish Industries 1988 Feb. 15 describes a tangled mass of randomly intertwined flat undulating elastic filaments which is intended for use as a substrate for developing prelarvae of salmon and similar fishes. The tangled mass of filaments described in patent SU 1,373,383-A to Pacific Fish Industries 1988 Feb. 15 is not intended to attract free living mobile animals away from competitive environments as is the case with harborages of the present invention but is, instead, intended to retain the developing pre-larvae of fishes which have been deposited into the tangled mass of filaments by their mother or by means of some other agent such as man. In addition, since the mass of filaments described in patent SU 1,375,383-A to Pacific Fish Industries 1988 Feb. 15 is intended for use with fish eggs which lack organs with which to sense the surrounding environment, patent SU 1,375,383-A to Pacific Fish Industries 1988 Feb. 15 fails to anticipate the importance of sensory perception of openings and their sizes and relationships to the effective exploring distances of the target animals as is made apparent in the case of animal harborages of the present invention. Furthermore, the mass of filaments described in patent SU 1,373,383-A to Pacific Fish Industries 1988 Feb. 15 is not intended to retain free living mobile animals within its structure as is the case with harborages of the present invention but is, instead, intended to encourage the developing fish to escape from the mass of filaments back into the outside environment. Moreover, the mass of filaments described in patent SU 1,373,383-A to Pacific Fish Industries 1988 Feb. 15 is intended to move with currents in the water and is not designed to be stable on the substrate as are harborages of the present invention. Those skilled in the biology of crawling animals will appreciate the importance of the stability of a harborage on the substrate to the attractiveness of the harborage to target crawling animals. Furthermore, the mass of filaments described in patent SU 1,373,383-A to Pacific Fish Industries 1988 Feb. 15 is not suitable for use with an adhesive as are animal harborages of the present invention. Those skilled in the art of pest control will appreciate that addition of an adhesive to the flexible mass of filaments described in patent SU 1,373,383-A to Pacific Fish Industries 1988 would stick the filaments together, thereby eliminating the openings and rendering the mass ineffective as a harborage. Finally, patent SU 1,373,383-A to Pacific Fish Industries 1988 Feb. 15 does not anticipate use of the disclosed harborage for control of crawling animals such as insects and rodents and as an artificial habitat for pet rodents.

Importance of Harborage Dimensions

Many students of insect and rodent behavior and those skilled in the arts of insect and rodent control suspect that there is a relationship between the dimensions of harborages and their effectiveness in attracting and holding various sizes of insects and rodents. For example, it is well known to those skilled in the art of rodent control that rodents prefer to enter harborages with openings approximating the cross sectional diameters of their bodies while preferring to feed within harborages or stations which allow them to sit up while eating.

Nevertheless, discussions of preferred harborage dimensions in the prior art have failed to recognize the importance of the dimension of depth as a factor determining the acceptability of a harborage to target animals and have considered only the height and width of the total harborage and the size and shape of only the external openings. Surprisingly, the dimension of depth has been found to be an important contributor to the success of harborages of the present invention. As an example of a discussion of harborage dimensions in the prior art, U.S. Pat. No. 4,395,842 to Margulies 1983 Aug. 2 gives a range of 4 to 10 mm for the height of exterior openings and a range of about 10 to 20 mm for the width of suitable exterior openings.

In addition to failing to consider the dimension of depth, studies of harborage dimensions in the prior art have also failed to recognize and appreciate the importance of the distances between both the exterior and interior openings of harborages and the number and arrangement of openings perceived by animals both before entering and after entering harborages. Surprisingly, the closeness of alternative openings and their spatial arrangement both on the exterior and in the interior of harborages have been found to be important contributors to the success of harborages of the present invention.

Moreover, discussions of preferred harborage dimensions in the prior art have defined the preferred dimensions of a harborage in absolute terms such as millimeters and have failed to recognize that a better method for determining the preferred dimensions of a harborage is to measure the critical dimensions in relation to the body size of the target animals and to the distances that target animals can explore and perceive before and after entering a harborage. The importance of defining the dimensions of harborages in terms of the body sizes and exploratory capabilities of the target animals has been recognized in the present invention.

As an example of a discussion of harborage dimensions in the prior art, U.S. Pat. No. 4,395,842 to Margulies 1983 Aug. 2, American roaches are said to be most likely to enter an opening which is about 19 mm to about 22 mm across whereas German roaches are said to be most likely to enter an opening about 5 mm to about 10 mm across. However, Mizuno and Tsuji 1974 Japanese Journal of Sanitary Zoology Volume 24 Number 3 pages 237-240 report that not all roaches of a given species prefer openings of the same size and that there are, in fact, clear differences between the heights of rectangular harborages preferred by adult roaches as opposed to those preferred by earlier developmental stages of American, German and Japanese roaches.

Importance of Effective Exploring Distance

It will therefore be clear to those skilled in the art that a comprehensive description of the relationships between body size and optimal harborage dimensions has not yet been developed f or insects, rodents and other crawling animals. Recent reviews in the prior art do not even mention the relationships between the sizes and exploratory abilities of target animals and the dimensions of harborages most suitable for them; particularly the importance of the number, depth and arrangement of openings that can be perceived by the target animals both before and after entering harborages. Surprisingly, the number, depth and arrangement of openings that can be perceived by the target animals both before and after entering harborages have been found to be important to the success of harborages of the present invention.

The distance that target animals can explore and perceive before entering and after entering a harborage of the present invention is termed the effective exploring distance. The effective exploring distance as considered in the present invention is important to the success of any animal harborage, including harborages of the present invention. It will be understood by those skilled in the art that effective exploring distance will vary among different types of crawling animals, being different among different species of roaches and other insects, and among different species of mice and other rodents. It will be further understood that effective exploring distance for a given type of animal will also depend upon such factors as the age, size, sex, reproductive condition and the locations and sensitivities of the sensory organs of the target animal. Results obtained with harborages of the present invention show that animals with larger effective exploring distances prefer harborages with greater absolute depths while animals with smaller effective exploring distances prefer harborages with lesser absolute depths. Although the preferred depths are different in the two cases when measured in absolute terms, the preferred depths may be substantially similar when measured in relative terms, for example, in terms of effective exploring distance or body length. Thus, minimally acceptable harborage dimensions for larger animals of the same body type, such as older roaches for example, will be larger than minimally acceptable harborage dimensions for smaller animals of the same body type such as younger roaches. Furthermore, it will be clear to those skilled in the art that a substantially similar relationship will hold between effective exploring distances and the sizes of adult and immature mice and other rodents.

Importance of Flexibility

In addition to failing to recognize the importance of the preferred depth of an animal harborage and its relationships to animal size, exploring reach and minimal harborage size, studies in the prior art have also failed to recognize the value of a flexible harborage as exemplified in the present invention. The exteriors of harborages described in the prior art are relatively rigid and are not intended to be flexed and formed to fit into irregular spaces and around moving parts of mechanical equipment and the like as is described in the present invention. It is well known to homeowners, pest control operators, farmers and others who use harborages of the prior art that compressing or bending harborages of the prior art will damage them and reduce their effectiveness. Surprisingly, harborages of the present invention retain their effectiveness after being bent and compressed.

OBJECTS OF THE INVENTION

Accordingly, a primary object of the present invention is to provide an improved harborage that is more attractive to target animals which crawl in search of shelter and more particularly to crawling arthropods such as roaches and other insects and to crawling mammals such as rats, mice and hamsters.

Another object is to provide a harborage that is less hazardous to use for control of roaches and the like than are harborages of the known art.

Another object is to provide a harborage that is manufactured from natural, biodegradable components.

Another object is to provide a harborage that is highly effective for control of insects such as roaches and the like.

Another object is to provide a harborage that is highly attractive to young roaches.

Another object is to provide a harborage that is less hazardous to use for control of rats and mice and the like than are harborages of the known art.

Another object is to provide a harborage that is highly effective for control of rats and mice and the like.

Another object is to provide a harborage that is highly effective for control of the endoparasites and ectoparasites of rats and mice and the like.

Another object is to provide a harborage that is well accepted as a habitat by rats, mice, hamsters and the like.

Another object is to provide a harborage that retains adhesives at an effective degree of tackiness without running or dripping and over a wide range of temperatures and humidities.

Another object is to provide a harborage that is highly effective for control of roaches and the like in high temperature environments such as around ovens, furnaces, incinerators and the like.

Another object is to provide a harborage that can be used effectively in irregular spaces.

Another object is to provide a harborage that can fit snugly into a wide range of openings such as under and around appliances and the like.

Another object is to provide a harborage that can be used effectively in contact with moving parts of machinery and equipment.

Another object is to provide a harborage that can be expanded into a larger, more complex structure by the addition of modular components.

Another object is to provide a harborage that is easy to clean.

Another object is to provide a harborage that combats urine and other pet odors.

Another object is to provide a harborage which is simple in construction and economical to produce.

Further objects and advantages of the present invention will become apparent from a consideration of the ensuing description of it.

SUMMARY OF THE INVENTION

These and other objects are achieved by the use of porous solids of the present invention as harborages wherein the target animals are continuously confronted by a multiplicity of attractive openings arrayed in three dimensions. This three dimensional array of attractive openings is presented to the target animals in such a way that the animals can perceive at least three sets of openings at increasing distances, thereby increasing the attractiveness of the harborage. Additionally, the arrangement of the openings in the harborage of the present invention makes the harborage more attractive to target animals by providing them with a gradual gradient in critical environmental factors such as light, temperature and humidity. This gradual shift between the less attractive exterior and the more attractive interior helps to draw the animals deeper into the harborage.

DESCRIPTION OF THE PREFERRED EMBODIMENTS

This invention relates to the use of certain porous solids as devices for attracting animals which crawl in search of shelter and, more particularly, to crawling arthropods such as roaches and other insects and to crawling mammals such as mice, rats and hamsters. The harborage of the present invention is surprisingly attractive and effective despite striking differences in construction from harborages of the prior art.

Figure 1:
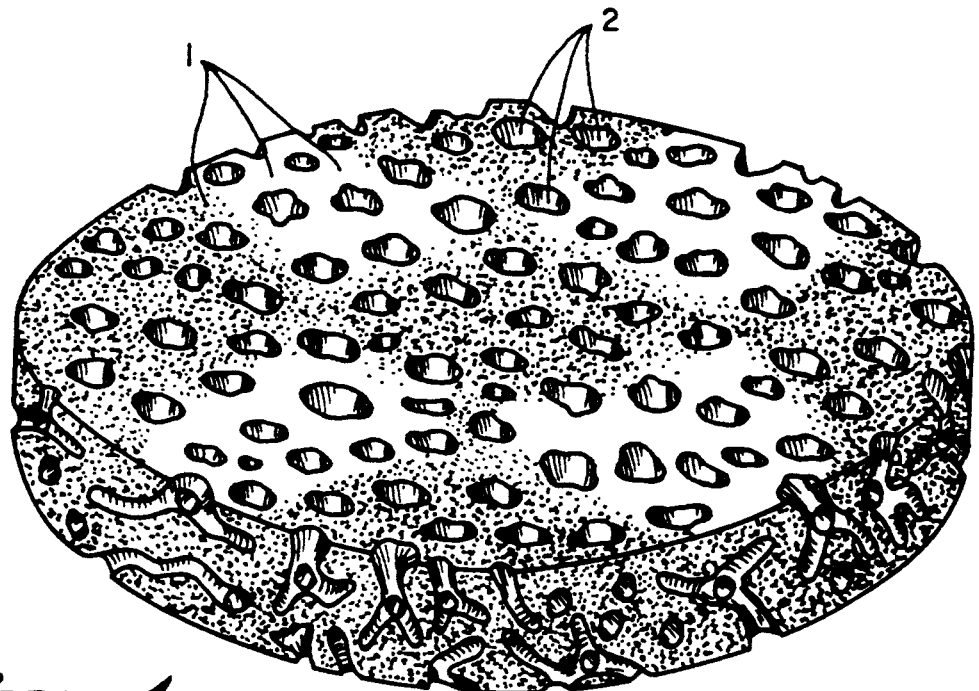
FIG. 1 shows a perspective view of a basic version of a terrestrial animal harborage comprised of a porous solid of the present invention.
Figure 2:
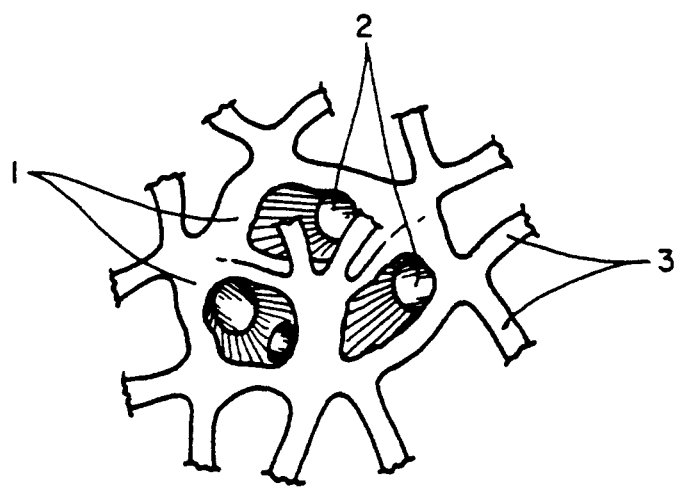
FIG. 2 shows a perspective view of a basic version of the cage, an internal cavity of the terrestrial animal harborage of the present invention.

It will be understood from consideration of the previous examples and Figs that a harborage of the present invention of any desired size and shape may be constructed by assembling the required components from the group consisting of web segments 3, webs 1 and cages. It will be further understood that the color, opacity, dimensions, surface features, tensile strength and other physical and chemical properties of a harborage of the present invention and its components may be varied in such a manner as to produce cages of different dimensions and cages and harborages with openings of differing sizes. FIG. 2 is intended for illustrative purposes only and is not intended to limit the number, size and shape of openings 2 which may be included in a cage, the number, size and shape of webs 1, and the number, size and shape of web segments 3.

Those skilled in the arts of pest control and pet management will appreciate that a harborage of the present invention can be used in the same fashion as stations, traps and artificial habitats of the prior art.

It will be further understood by those skilled in the art that the minimum length and thickness of the webs in a particular embodiment of the present invention will depend upon the physical properties of the web material such as tensile strength, rigidity and the like and the behavioral preferences of the target animals for thickness, surface texture, color, stability and the like of the web material.

In a preferred embodiment, a harborage of the present invention comprising a single body contains within itself all of the webs 1 and openings 2 of the harborage.

It will be understood that a variety of useful embodiments of the harborage of the present invention may be constructed using a plurality of components such as webs 1, web segments 3, cages and partial cages in various combinations and joined together by suitable means.

In another preferred embodiment, a harborage of the present invention comprises a three-dimensional array of openings 2 of a sufficient size, number and arrangement so as to present target animals with a minimum of three openings 2 through which the target animals may attempt to crawl at any time during which they are in contact with the harborage, while both inside the harborage and outside it.

The maximum number of openings 2 presented by a harborage of the present invention is defined by the minimum length and thickness of the webs 1 which surround the openings 2 in the harborage, and the effective exploring distance of the target animals.

The effective exploring distance as considered in the present invention is important to the success of animal harborages and has not been appreciated by the prior art. It will be understood by those skilled in the art that effective exploring distance varies among different species of roaches, mice and other animals and depends upon such factors as their size, sex, reproductive condition and the locations and sensitivities of their sensory organs.

It will be further understood that the preferred dimensions of the cage in harborages of the present invention are likewise defined by the dimensions of the webs and the maximum exploring reach of the target animals.

Another preferred embodiment of the present invention comprises a harborage that presents target animals with at least two cages in at least one dimension.

Another preferred embodiment comprises a harborage having at least one dimension equal to the effective exploring distance of the target animal.

Surprisingly, it has been found in the present invention that an array of openings of differing sizes enhances the attractiveness of harborages to crawling animals, such as insects, rodents and the like. This improvement in acceptability is evidenced by the ability of a single harborage of the present invention constructed with openings of different sizes to attract different sizes of roaches with equal effectiveness.

It will be understood from the previous examples that the improved harborage of the present invention may be used alone as a habitat for pet rodents such as rats, mice, hamsters and the like. Surprisingly, harborages constructed according to the present invention are highly attractive to target animals such as roaches, mice, rats, hamsters and the like. Such animals remain inside harborages of the present invention without the use of adhesives, baits or attractants, often turning back when they reach an exit hole and continuing to explore the interior of the harborage.

In another preferred embodiment, the harborage of the present invention contains an odorant, odor mask, deodorant or odor neutralizer to combat urine and other pet odors.

In another preferred embodiment, the harborage of the present invention comprises an assembly of modular components assembled by appropriate means. Such modular components comprise one or more members of the group consisting of cages, webs and web segments, which components may be disassembled easily to facilitate cleaning of the harborage.

It will be understood that the surface of all or part of the harborage of the present invention may be used for the purpose of trapping roaches, rats, mice and the like according to methods familiar to those skilled in the art of pest control.

The increased complexity of the interior surface of the harborage of the present invention requires less adhesive than adhesive traps of the known art and reduces leaking and running of adhesives at high temperatures and humidities.

In another preferred embodiment, a substantial part of the harborage of the present invention is comprised of one or more different kinds of baits. Rodents have been observed to gnaw the edges of the webs 1 in harborages of the present invention, thereby making all or part of harborages of the present invention surprisingly useful as carriers of baits.

In another preferred embodiment, the harborage of the present invention incorporates one or more suitable biologically active agents chosen from the group consisting of insecticides, rodenticides, parasiticides and attractants by processes known to those skilled in the art, including such methods as dusting, dipping and spraying.

In another preferred embodiment, the harborage of the present invention is constructed from one or more members of the group of flexible substances including rubber, flexible plastics and the like that are familiar to those skilled in the art. Such a flexible harborage is suitable for fitting snugly under appliances and the like and in contact with moving parts of machinery.

In another preferred embodiment, the harborage of the present invention is constructed from the group consisting of various reticulated porous ceramics including lithium alumina silicate, mullite and otherwise suitable substances known to those skilled in the art. Such harborages of the present invention are suitable for control of roaches and the like around ovens, furnaces, incinerators and the like. All or part of such harborages may be treated with a heat resistant pesticide such as boric acid by methods known to those skilled in the art.

In another embodiment, a harborage of the present invention may be fitted with a lid or bottom with means for attachment to walls, ceilings, underside of shelves and the like.

In another preferred embodiment, a harborage of the present invention is combined with a harborage of the known art in such a manner as to allow a rodent station to control cockroaches and to allow a roach station to kill rodents and rodent ectoparasites.

In another preferred embodiment, a harborage of the present invention comprises a maze or filter that traps the target animals.

In another preferred embodiment, a harborage of the present invention is constructed with openings of a size that excludes larger animals while allowing smaller, younger members of the population of the same species to enter. A harborage of this type can be used to protect the young of pet rodents from predation from larger animals. Similarly a harborage of this type can decrease the time needed to control a pest population by controlling smaller, less dominant individuals which would otherwise not be eliminated until after the larger, more dominant members of the pest population had been removed by bait stations and the like of the prior art.

While the above descriptions contain many specificities, these should not be construed as limitations on the scope of the present invention, but rather as exemplifications of several preferred embodiments thereof. Many other variations are possible.

The following examples are intended to illustrate, but not limit the present invention.

EXAMPLE I

In order to demonstrate the effectiveness of a animal harborage of the present invention suitable for use under conditions of high temperature, a rigid, cylindrical harborage of the present invention was constructed by dipping a mullite (Hi-Tech Ceramics Inc. P.O. Box 1105, Alfred, N.Y. 14802) ceramic matrix 76 mm in diameter by 10 mm in thickness in an insecticide solution of 500 parts per million of 1-(4-chlorophenyl)-3-(2,6-difluorobenzoyl)urea (diflubenzuron) insecticide in water. The harborage was then placed in a container with egg cases of German roaches.

When the eggs hatched, the young roaches readily entered the harborage. The harborage contained approximately 45 openings per sq cm with an average opening diameter of 1 mm of which openings approximately 30 percent were sufficiently large to allow the roaches to crawl through them, resulting in a total number of useable openings many thousands of times greater than those presented by harborages of the known art.

The webs of the harborage were approximately circular in cross section, generally 1 to 2 mm in length and 0.5 to 1 mm in diameter. These web lengths were generally 0.5 to 1.0 body lengths for first instar German roaches. The web diameters were generally 0.25 to 0.5 body lengths for first instar German roaches. The cages of the harborage were roughly spherical and had diameters ranging from about 2 mm to about 8 mm. These diameters are roughly equivalent to 1 to 4 body lengths for first instar German roaches. All of the young roaches were killed by the harborage before reaching their second instar.

In addition to providing the benefit of effective operation after exposure to high temperatures, the harborage of this embodiment also provides the additional advantages of a harborage that is surprisingly attractive to first instar roaches, a life stage that is not readily attracted to harborages of the prior art. The harborage is also less hazardous than harborages of the known art, is highly effective, is capable of retaining adhesives better than harborages of the prior art, is capable of being used in computers, microwave ovens and other electrical equipment, can be expanded into larger more complex structures by the addition of modular components and is simple in construction and economical to produce.

EXAMPLE II

In order to demonstrate the effectiveness of a flexible harborage of the present invention, an irregularly shaped, flexible harborage was constructed by treating the interiors of six pieces of polystyrene packing with an insecticide solution of 0.1 percent isopropyl(E,E)-(RS)-11-mehoxy-3,7,11-trimethyldodeca-2,4-dienoate (methoprene) insecticide sterilant and ectoparasiticide, 0.075 percent perchloro-1,1'-bicyclopenta-2,4-diene (dienochlor) miticide, and 0.57 percent (1RS,3RS;1RS,3SR)-2,2-dimethyl-3-(2-methylprop-1-enyl)=cyclopropanecarbozylate (resmethrin) repellent insecticide. The packing pieces were each approximately 50 mm long by 20 mm wide by 3 mm thick and contained two oval orifices approximately 13 mm in maximum diameter. The treated packing pieces were then glued together so as to form a single irregular harborage of the present invention. Twenty untreated packing pieces were then glued to the exterior of the mass of treated pieces to create a larger irregular harborage with an untreated exterior and a insecticidal interior.

The larger harborage was readily compressible and resilient, returning to its original form after the pressure was withdrawn. The resilient harborage was then placed in a container with 5 third instar German roaches.

The harborage presented 1 opening per 12 to 15 mm resulting in more than 100 openings of a size that could be entered by the roaches. The webs were roughly rectangular in cross section, 3 mm thick and 20 mm long. These web lengths were approximately equal to 2 body lengths for third instar German roaches. The web diameters were approximately equal to 0.3 body lengths for third instar German roaches. The cages of the harborage were roughly spherical and had diameters ranging from about 20 mm to about 40 mm. These diameters are equivalent to about 2 to about 4 body lengths for third instar German roaches.

The roaches remained outside the harborage for two weeks during which time the repellent action of resmethrin decreased. The roaches then entered the harborage readily. All of the resulting adult roaches were sterilized by exposure to the harborage.

In addition to providing the benefit of a flexible harborage, the harborage of this embodiment was also less hazardous to children and pets than harborages of the known art. Moreover, the harborage was highly effective, capable of being used in irregular spaces, capable of fitting snugly into a wide range of spaces, capable of effective use in contact with moving parts of machinery and equipment, capable of being expanded into larger, more complex structures by the addition of modular components, simple in construction and economical to produce.

EXAMPLE III

In order to demonstrate the effectiveness of a harborage of the present invention which has been impregnated with an insecticide, 50 rectangular pieces of plastic flea collar approximately 3 mm by 3 mm by 20 mm impregnated with 9.4 percent propoxur insecticide were placed together so as to form a harborage of the present invention having an irregular shape and approximately 40 mm in maximum diameter. Approximately 70 percent of the exterior of the harborage was covered with masking tape which served to hold the plastic pieces in place.

There were approximately 4 openings of various sizes per cm on the exterior surfaces of the harborage that were not covered with tape. The sides of the openings were straight, resulting in openings that were shaped like polygons such as triangles, rectangles and the like. The webs were rectangular in cross section, approximately 3 mm wide by 20 mm long by 3 mm deep. These web lengths were approximately equivalent to 10 body lengths for first instar German roaches. The web diameters were approximately 1.5 to 2 body lengths for first instar German roaches. The cages of the harborage were approximately cubical and had diameters of approximately 3 mm. This diameter is approximately equivalent to 1.5 body lengths for first instar German roaches. The harborage contained more than 100 openings of various sizes.

The harborage was placed in a container with 5 first instar German roaches. All of the roaches entered the harborage and died within one hour. Two of the roaches died inside the harborage.

In addition to providing the benefit of a rapidly acting toxic harborage, the harborage of this embodiment was also highly attractive to young roaches, capable of incorporating a wide variety of biologically active agents, capable of effective use in irregular spaces, capable of use in a wide range of spaces such as under and around appliances, capable of being expanded into larger, more complex structures by the addition of modular components, simple in construction and economical to produce.

EXAMPLE IV

In order to demonstrate the effectiveness of a harborage of the present invention when constructed of natural, biodegradable materials, a section of dried loofa gourd was cut so as to give a harborage of the present invention of roughly triangular exterior dimensions approximately 25 mm thick and approximately 65 mm in diameter. A globular piece of peanut butter approximately 5 mm in diameter was placed as a bait in the center of the section of loofa gourd.

The webs of the harborage were circular to flatly oval in cross section, approximately 3 mm to 30 mm in length and varied from approximately 0.5 to 2.0 mm in diameter. These web lengths were approximately 0.38 to 3.75 body lengths for second instar American roaches and approximately 0.25 to 2.5 body lengths for third instar American roaches. The web diameters were approximately 0.07 to 0.25 body lengths for second instar American roaches and approximately 0.04 to 0.16 body lengths for third instar American roaches.

The cages of the harborage were irregular in size and shape. The maximum dimensions of the cages varied widely ranging from approximately 2 mm to approximately 25 mm. These dimensions are equivalent to approximately 0.25 to 3.13 body lengths for second instar American roaches and approximately 0.16 to 2.08 body lengths for third instar American roaches. More than 100 openings of a size suitable for entry were present in the harborage.

Five second and third instar American roaches were placed in a container with the harborage. The roaches entered the harborage almost immediately and continued to hide in and explore it for several days, feeding on the peanut butter and climbing through the cages formed by the dried loofa fibers.

In addition to providing the benefit of a harborage composed of natural, biodegradable materials, the harborage of this embodiment also provided the additional advantages of increased attractiveness to a variety of sizes of target animals, including young roaches, less hazardous in use than harborages of the known art, and better an more economical retention of adhesives. Furthermore, the harborage capable of effective use in irregular spaces and of fitting snugly into a wide range of openings and was capable of being expanded into a larger structure by the addition of modular components. Moreover, the harborage was simple in construction and economical to produce.

EXAMPLE V

In order to demonstrate the effectiveness of a harborage of the present invention as an artificial habitat for small rodents, 30 cardboard tubes approximately 2 mm thick, 25 mm in diameter and 20 mm in depth were glued together to produce a roughly rectangular harborage of the present invention.

The webs of the harborage were rectangular in cross section, approximately 2 mm thick, and approximately 20 mm long. These web lengths are approximately 0.2 to 0.3 body lengths for an adult house mouse. The web cross sections were approximately 0.02 to 0.03 body lengths for an adult house mouse.

The openings were curvilinear portions of circles of various sizes, more than 40 of which exceeded 13 mm inch in minimum diameter and could be entered by an adult house mouse.

The cages of the harborage had diameters ranging from about 20 mm to about 80 mm. These diameters are equivalent to about 0.33 to about 0.44 body lengths for an adult house mouse.

The harborage was placed in a cage along with a plastic bait station designed for house mice and of a type described in U.S. Pat. No. 4,637,162 to Sherman, 1987 Jan. 20. This particular station is considered by those skilled in the art to be a highly effective bait station. The mouse investigated the openings of the station of the known art but did not enter it. The mouse then investigated the harborage of the present invention, squeezed through one of the initial openings and then began to crawl through the harborage, poking its head out from time to time and then returning to explore the harborage. This behavior continued for more than an hour, after which the mouse began gnawing at the edges of the openings of the harborage of the present invention in an apparent effort to enlarge the cages and improve the suitability of the harborage as a nesting or resting place.

In addition to providing the benefit of an effective artificial habitat for small rodents, the harborage of this embodiment also provided the additional advantages of being more attractive to small rodents than harborages of the known art, less hazardous to use than harborages of the known art, highly effective for control of rats and mice, highly effective for control of the ectoparasites and endoparasites of rats and mice, capable of retaining adhesives more effectively than harborages of the known art, capable of effective use in irregular spaces, capable of being expanded into larger more complex structures by the addition of modular components, easy to clean, capable of incorporating agents to combat urine and other pet odors, simple in construction and economical to produce.

Other embodiments of the present invention will be apparent to those skilled in the art. Accordingly, the scope of the invention should be determined not by the embodiments described, but by the appended claims and their legal equivalents.

I claim:

1. A manmade device for attracting and retaining crawling terrestrial animals, consisting of at least one unitary porous solid, said at least one solid consisting of a multiplicity of webs, said webs being connected at their extremities to form a multiplicity of external openings and internal chambers, the size of said openings and chambers being sufficient to admit said animals, and the size of said openings and chambers being determined by the size of said webs, and said openings and said chambers being interconnected in a substantially random manner throughout said at least one solid, so that said animals perceive three or more of said openings and said chambers while said animals are in contact with said webs, and said device being attractive to said animals by virtue of its morphology alone and without the need of baits, chemical lures or pheromones, and said device bringing said animals into contact with at least one material suitable for killing, trapping or sterilizing said animals, and said at least one material being placed on or within said device, and said at least one material not occurring naturally with said device.

2. The device of claim 1 wherein said webs are ceramic.

3. The device of claim 1 wherein said webs are plastic.

* * * * *